(12) United States Patent
Ullah et al.

(10) Patent No.: US 10,039,280 B1
(45) Date of Patent: Aug. 7, 2018

(54) HERBICIDAL FLURIDONE COMPOSITIONS

(71) Applicant: SePRO Corporation, Carmel, IN (US)

(72) Inventors: Hamid Ullah, Whitakers, NC (US);
Tyler J. Koschnick, Westfield, IN (US);
Mark A. Heilman, Carmel, IN (US)

(73) Assignee: SePRO Corporation, Carmel, IN (US)

( * ) Notice: Subject to any disclaimer, the term of this patent is extended or adjusted under 35 U.S.C. 154(b) by 0 days.

(21) Appl. No.: 14/091,898

(22) Filed: Nov. 27, 2013

Related U.S. Application Data

(63) Continuation of application No. 14/010,015, filed on Aug. 26, 2013, now abandoned.

(60) Provisional application No. 61/693,274, filed on Aug. 25, 2012.

(51) Int. Cl.
*A01N 43/40* (2006.01)
*A01N 25/04* (2006.01)
*A01N 25/30* (2006.01)

(52) U.S. Cl.
CPC ............. *A01N 25/04* (2013.01); *A01N 25/30* (2013.01); *A01N 43/40* (2013.01)

(58) Field of Classification Search
CPC ......... A01N 43/40; A01N 25/04; A01N 25/30
See application file for complete search history.

(56) References Cited

U.S. PATENT DOCUMENTS

| | | | |
|---|---|---|---|
| 4,318,730 A | 3/1982 | Mori et al. | |
| 5,206,021 A | 4/1993 | Dookhith et al. | |
| 6,071,857 A | 6/2000 | Vogt et al. | |
| 6,348,434 B1 | 2/2002 | Schmidt | |
| 6,383,984 B1 | 5/2002 | Aven | |
| 6,444,618 B1 | 9/2002 | Aven et al. | |
| 6,566,308 B1 | 5/2003 | Aven | |
| 6,713,433 B2 | 3/2004 | Jimoh | |
| 6,890,886 B2 | 5/2005 | Policello et al. | |
| 8,044,059 B2 | 10/2011 | Hopkins et al. | |
| 2002/0119891 A1 | 8/2002 | Netherland | |
| 2003/0060514 A1 | 3/2003 | Aven | |
| 2006/0276337 A1 | 12/2006 | Sixl et al. | |
| 2007/0197391 A1 | 8/2007 | Clark et al. | |
| 2008/0254983 A1 | 10/2008 | Panayi et al. | |
| 2009/0105073 A1* | 4/2009 | Taranta et al. | 504/100 |
| 2009/0215797 A1* | 8/2009 | Hopkins et al. | 514/259.31 |
| 2009/0298691 A1 | 12/2009 | Koschnick et al. | |
| 2009/0325803 A1 | 12/2009 | Koschnick | |
| 2010/0016160 A1 | 1/2010 | Bettarini et al. | |
| 2010/0234230 A1 | 9/2010 | Fowler | |

OTHER PUBLICATIONS

Frontline* 2,4-D B Emulsifiable Concentrate Herbicide Material Safety Data Sheet. Dow AgoSciences. Product Code No. 163687. Effective date Jul. 24, 2007.
http://en.wikipedia.org/wiki/Colloid. Printed Aug. 17, 2012, pp. 1-11.
http://en.wikipedia.org/wiki/Dynamic_light_scattering. Printed Aug. 17, 2012, pp. 1-6.
http://en.wikipedia.org/wiki/Emulsion. Printed Aug. 10, 2012, pp. 1-7.
http://en.wikipedia.org/wiki/Suspension_(chemistry). Printed Aug. 10, 2012, pp. 1-3.
Sonar Genesis Aquatic Herbicide Material Safety Data Sheet. SePRO Corpoaration. EPA Registration No. 67690-54. Issued Aug. 15, 2011.
Package insert for Sonar Genesis Aquatic Herbicide, Concentrated Formulation. SePRO Corporation. EPA Registration No. 67690-54, 12 pages, (2010).
McCowen, Max C. et al., "Fluridone, A New Herbicide for Aquatic Plant Management." J. Aquat. Plant Manage. 17:27-30. 1979. 4 pages.

\* cited by examiner

*Primary Examiner* — John Pak
*Assistant Examiner* — Nathan W Schlientz
(74) *Attorney, Agent, or Firm* — Woodard, Emhardt, Moriarty, McNett & Henry LLP

(57) ABSTRACT

Described are preferred methods and compositions useful for controlling aquatic weeds that involve the use of fluridone. Preferred herbicidal compositions include fluridone in a formulation that also comprises an organic solvent and an emulsifying surfactant system.

16 Claims, 1 Drawing Sheet

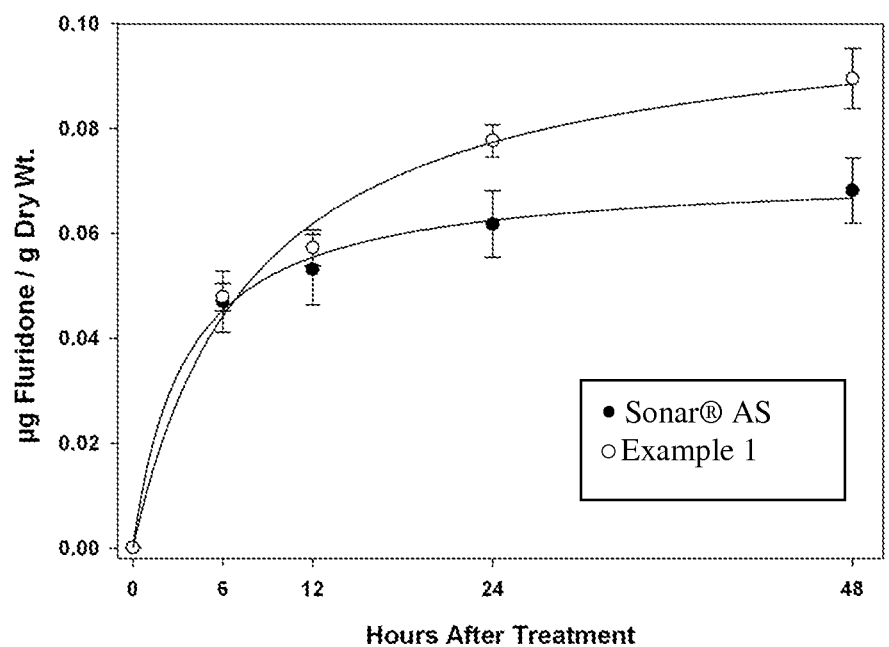

HERBICIDAL FLURIDONE COMPOSITIONS

CROSS REFERENCE TO RELATED APPLICATIONS

This application is a continuation of U.S. application Ser. No. 14/010,015, filed on Aug. 26, 2013, which claims the benefit of priority to U.S. Provisional Application No. 61/693,274, filed Aug. 25, 2012, both of which are hereby incorporated by reference in their entirety.

BACKGROUND

The present invention relates generally to fluridone-related compositions and methods that are useful, for example, in herbicidal applications.

As further background, aquatic plants very commonly arise as undesired weeds in waters and wetlands in the United States of America and elsewhere. Three such exotic weeds are hydrilla, curlyleaf pondweed, and watermilfoil, including Eurasian watermilfoil. These weeds often present problems in ponds, lakes, and other water bodies.

Fluridone is a bleaching herbicide that has been used in the control of aquatic weeds. Commercially, fluridone is available as a liquid formulation in a suspension concentrate form, in which fluridone solids are suspended in an aqueous carrier formulation. Fluridone has very limited solubility in a wide variety of solvent systems, and efforts to develop and market this agent have focussed on relatively highly concentrated solid suspension concentrates or solid forms.

Formulation stability is a key factor in the successful development of herbicidal formulations. The development of storage-stable, flowable liquid formulations has presented many difficulties over the years. Attempts to prepare such formulations meet with a variety of failures, commonly involving phase separation. A variety of phase separations may occur including as examples crystallization, sedimentation, creaming, Ostwald ripening, and the like. Moreover, in the case of so-called "emulsifiable concentrate" formulations, solubility issues relative to the active agent and the organic solvent system used create difficulties. For example, it can be difficult to develop an organic solvent system that will stably solvate the herbicidal active agent at acceptable levels during storage and yet form a beneficial emulsion when added to water that effectively delivers the active agent to the target plants.

In view of the background in this area, needs exist for improved and/or alternative formulations of fluridone and other like herbicidal agents.

SUMMARY OF THE INVENTION

In certain aspects, the present invention provides herbicidal compositions that include fluridone, an organic solvent system and an emulsifying surfactant system, and that exhibit the capacity to form emulsions when added to water. Such compositions can deliver the fluridone in a highly effective manner when applied (alone or combined with another material such another liquid medium) to a plant or plant-growth-supporting environment, such as a body of water, soil or a soil surface, where herbicidal activity is desired. In certain aspects, such application is to a body of water to control aquatic weeds. Application of the preferred herbicidal compositions as described herein can lead to rapid uptake of the fluridone by weeds.

In one aspect, the invention provides a herbicidal composition that includes fluridone, a water-immiscible organic solvent component that includes one or more water-immiscible organic solvents, a water-miscible organic solvent component that includes one or more water-miscible organic solvents, and an emulsifying surfactant system. The surfactant system can include one, or a plurality of, surfactants, which can be anionic, cationic, nonionic, or combinations thereof. The water-immiscible organic solvent component preferably includes one or more N,N-dimethyl alkylamides such as N,N-dimethyl octamide (N,N-dimethyloctanamide), N,N-dimethyl decamide (N,N-dimethyldecanamide), or mixtures thereof. The water-miscible organic solvent component preferably includes propylene glycol. The emulsifying surfactant system preferably includes at least one anionic surfactant and at least one nonionic surfactant. The fluridone can constitute about 3% to about 15% by weight of the composition, more preferably about 3% to about 9% by weight. Any one of the above features or any combinations thereof can also be combined with one, some or all of the following features:

the water-miscible organic solvent component can constitute about 20% to about 60% by weight of the composition, more preferably about 35% to about 55% by weight;

the water-immiscible organic solvent component can constitute about 20% to about 60% by weight of the composition, more preferably about 20% to about 45% by weight;

the composition can be substantially free from water;

the composition can be a substantially homogeneous solution;

the composition can be capable of forming an emulsion when combined with water, more preferably where the emulsion is a clear (i.e. non-cloudy) liquid;

the water-immiscible solvent component can be constituted at least about 50% by weight of one or more N,N-dimethyl alkylamides, preferably at least about 75% by weight, and more preferably at least about 90% by weight; the one or more N,N-dimethyl alkyamides in any of the features in this paragraph can comprise one or both of N,N-dimethyl octamide and N,N-dimethyl decamide, or can be constituted at least 80%, or at least 90%, of one or both of N,N-dimethyl octamide and N,N-dimethyl decamide.

In additional aspects of the invention, provided are methods for treating plants or environments with fluridone, comprising applying to the plants or to their supporting environment (e.g. an aquatic or terrestrial environment) a herbicidal composition as defined above and/or elsewhere herein, or another composition prepared therefrom, e.g by combining the herbicidal composition with another substance such as an aqueous or other liquid medium. In preferred modes these methods are for controlling aquatic weeds in a body of water, and the herbicidal composition, or another composition prepared by combining the herbicidal composition with an aqueous or other liquid medium, is added to the body of water. Such addition can be accomplished in any suitable manner including injection of the herbicidal or other composition into the body of water.

Additional embodiments of the invention, as well as features and advantages thereof, will be apparent from the descriptions herein.

BRIEF DESCRIPTION OF THE DRAWING

FIG. 1 displays uptake of $^{14}C$ radiolabelled fluridone over time by apical hydrilla tissue when applied as a commercial aqueous suspension formulation known as Sonar@ A.S. or the formulation of Example 1.

DETAILED DESCRIPTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications, and such further applications of the principles of the invention as described herein being contemplated as would normally occur to one skilled in the art to which the invention relates.

As disclosed above, in certain of its aspects the present invention relates to herbicidal formulations that include fluridone, an organic solvent system and an emulsifying surfactant system. The organic solvent system typically includes a water-immiscible organic solvent component, and a water-miscible organic solvent component. The surfactant system can include one surfactant or more than one surfactant. In preferred forms the herbicidal compositions are substantially free from water (i.e. containing no more than 5% by weight water), more preferably essentially completely free from water, for example containing no more than 1% by weight water, or no more than 0.2% by weight water. Additionally or alternatively, the compositions can be substantially homogeneous solutions, and/or can be emulsifiable in water, in particularly desirable forms exhibiting the capacity to form clear liquid emulsions (as opposed to cloudy emulsions) when combined with water. Such clear liquid emulsions may be, in certain embodiments, microemulsions in which the dispersed phase liquid bodies, commonly referred to as droplets, are sufficiently small that the formed liquid medium is visible to the naked human eye (i.e. unassisted by optical instrumentation) as a clear solution.

The chemical fluridone, formally named (1-methyl-3-phenyl-5-[3-(trifluoromethyl)phenyl]-4(1H)-pyridone) is a known herbicide for use in the control of aquatic or terrestrial weeds. Fluridone is sold under the trade name SONAR®, available from SePRO Corporation, Carmel, Ind., in either liquid or pelleted (on clay) formulations. In aquatic systems, fluridone is a systematic herbicide that is absorbed from water by plant shoots and from hydrosoil by roots. It inhibits carotenoid synthesis which in turn enhances the degradation of chlorophyll. This produces a characteristic bleached appearance to susceptible plants.

Fluridone can be included in the herbicidal composition in any suitable amount. Fluridone amounts of at least 3% by weight in the herbicidal composition, and/or fluridone amounts no greater than about 15% by weight in the herbicidal composition, are contemplated in aspects of the invention. In regard to these weight percentages and the other weight percentages stated herein, the percentages are given as weight:weight percentages, unless stated otherwise or clear from context. Typically, the fluridone is included in the range of about 3% to about 15% by weight, preferably about 3% to about 11% by weight, more preferably about 5% to about 9% by weight. In certain embodiments, the fluridone is included in an amount of about 6% to 7% by weight. While these preferred ranges are relatively low compared to traditional herbicidal "concentrates" these ranges have been found by the inventors to provide highly beneficial and economic emulsifiable herbicidal compositions, with good storage stability and application properties.

As noted above, herbicidal formulations of the invention include an organic solvent system, typically including one or more water-immiscible organic solvents. Such water-immiscible organic solvents will usually be nonpolar. Illustrative water-immiscible organic solvents which may be used include for example aliphatic and aromatic hydrocarbons such as hexane, cyclohexane, benzene, toluene, xylene, mineral oil or kerosin or substituted naphthalenes, mixtures of mono- and polyalkylated aromatics; esters of plant oils such as alkyl (e.g. methyl) esters obtainable from medium chained fatty acids (e.g. having 5 to 20 carbon atoms) by esterification with alkanols or by transesterification of the corresponding plant oils preferably in the presence of a lipase; N-octyl-2-pyrrolidone (e.g. the commercially available product Agsolex® 8); or N-alkanoyl morpholines or mixtures thereof having the formula R—CO—Z where R is an alkyl group having 5 to 11 carbon atoms and Z is a 4-morpholinyl group (i.e. having its ring nitrogen atom bonded to the carbon of the adjacent —CO— group. A suitable N-alkanolyl morpholine solvent is available commercially under the trademark Jeffsol® AG1730, and is a mixture of N-alkanoyl morpholines from N-pentanoylmorpholine to N-undecanoyl-morpholine.

In certain preferred embodiments herein, the one or more water-immiscible organic solvents present in the herbicidal composition will include one or more N,N-dimethylalkyl amides such as N,N-dimethyloctamide, N,N-dimethyldecamide (these also known as N,N-dimethyloctanamide and N,N-dimethyldecanamide), or mixtures including them. Commercially available solvents under the tradenames Hallcomid M-8-10 or Genagen 4166 contain mixtures of N,N-dimethyloctamide (typically 50-65% by weight) and N,N-dimethyldecamide (typically 37-50% by weight), which can also contain minor amounts of N,N-dimethylhexamide and N,N-demethyldodecamide (typically less than 10% by weight total). In certain embodiments, any such N,N-dimethylalkyl amide, or N,N-dimethylalky amide mixture, can constitute at least about 50% by weight of the one or more water-immiscible solvents in the herbicidal composition, more preferably at least about 75% by weight, and even more preferably at least about 90% by weight. In addition or alternatively, where an N,N-dimethylalkyl amide solvent is used, such solvent can be constituted at least 90% by weight of N,N-dimethyl octamide, of N,N-dimethyl decamide, or of a mixture of N,N-dimethyl octamide and N,N-dimethyl decamide.

In other embodiments, N-alkanoyl morpholines or mixtures thereof as described above and/or N-octyl-2-pyrrolidone can be used as or in the one or more water-immiscible solvents, potentially in addition to N,N-dimethylalkyl amide(s) as described above.

Water-miscible organic solvent(s) that can be used in combination with the water-immiscible organic solvent(s) are typically polar aprotic organic solvents, for example having a dielectric constant of about 2.5 to about 4.0 at 25° C. Illustrative water-miscible organic solvents include cyclic amides and lactones, for example N-methylpyrrolidone, N-cyclohexylpyrrolidone and .gamma.-butyrolactone; alkyl lactates, for example isopropyl lactate; alkyl carbonates; alkylene carbonates such as propylene carbonate; polyethylene glycols; polyethylene glycol alkyl ethers; polypropylene glycols; polypropylene glycol alkyl ethers; cyclohexanone; dimethylsulfoxide; methyl isoamyl ketone; N-methyl-2-pyrrolidone; or mixtures thereof. A water-miscible organic solvent component of the herbicidal composition can include one or more water-miscible organic solvent compounds. In certain embodiments, the one or more water-miscible organic solvents includes, consists essentially, or consists of propylene glycol (1,2-propanediol), or is constituted at least about 50%, or at least about 75%, or at least about 90%, by weight, of propylene glycol. Where propylene glycol is included in combination with one or more additional water-miscible organic solvent compounds, those compounds can be selected from any one or any combination of such compounds disclosed herein, and/or others that are known.

The emulsifying surfactant system of the herbicidal composition will include at least one surfactant and typically a plurality of (two or more) surfactants. Such surfactant(s) can be anionic, cationic or nonionic in character. Surfactants conventionally used in the art of formulation and which may also be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Known surfactants include salts of alkyl sulfates, such as diethanolammonium lauryl sulfate; alkylarylsulfonate salts, such as dodecylbenzenesulfonate salts (e.g. the calcium salt); alkylarylsulfonic acids, such as dodecylbenzene sulfonic acid, alkyl and/or arylalkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; polyethoxylated alkylphenols; polyethylated fatty alcohols; alkyl benzenesulfonic acids; alkyl glycosides; ethoxylate/propoxylate block co-polymers such as a butyl ethoxylate/propoxylate block copolymer (e.g. commercially available under the trademark Toximul 8320), these preferably having an average molecular weight of less than about 5000; N,N-dimethylalkyl amides; glycols; alkylamines; triethanol amine; quarternary salts of amines; 2-ethyl-1-hexanol (adjuvant of surfactants); and mixtures thereof.

In certain preferred embodiments, the emulsifying surfactant system includes at least one anionic surfactant, especially dodecylbenzene sulfonic acid, and at least one nonionic surfactant, especially a butyl ethoxylate/propoxylate block copolymer.

In additional preferred embodiments, the emulsifying surfactant system includes at least one of, and potentially some or all of, a butyl ethoxylate/propoxylate block copolymer, dodecylbenzene sulfonic acid, 2-ethyl-1-hexanol, and triethanolamine.

In certain embodiments, the herbicidal composition will also include one or more antifoaming agents. Illustrative antifoaming agents which can be used include silicone derivatives such as silicone emulsions, for example a 30% silicon emulsion (e.g. commercial antifoam AF 30 IND), and silicone oils; perfluoroalkylphosphonic/perfluoroalkylphosphinc acids, in particular polydimethylsiloxanes, mixtures comprising perfluoro-($C_{16-18}$)-alkylphosphonic acids, and perfluoro-($C_{16-18}$)-alkylphosphinic acids. Silicone derivatives, and in particular silicone emulsions, or silicon oils, are preferred. The antifoaming agent(s) will typically be present in a relatively minor amount, for example less than about 2%, or less than about 1%, of the herbicidal composition.

In addition to the components set forth above, the herbicidal compositions of the invention may include one or more additional ingredients. Other additional ingredients may include, for example, one or more other pesticides (e.g. herbicides), dyes, stabilizers (e.g. 2-hydroxy-4-noctyloxybenzophenone), fragrances, viscosity-modifying additives, suspension aids, dispersants, and others. These additional ingredients, when present, typically together constitute a relatively low percentage by weight of the herbicidal composition, for example less than about 10% by weight in certain embodiments.

The ingredients of the herbicidal composition can be conventionally combined, with preference to form a homogenous solution. Conventional equipment as well as heating and agitating conditions, as necessary, can be employed. The formation of storage stable solutions, for example those that exhibit the capacity to remain clear solutions without any phase separation for a period of at least 30 days and more preferably at least a year when maintained at 25° C., are preferred. In another embodiment, the storage stable solution does not exhibit phase separation for a period of greater than one day or greater than one week when maintained at 25° C. The storage stable solution can be a yellow or pale yellow color. Such maintenance over time will typically be in a sealed, fluid-tight inert container. As well, herbicidal compositions that are emulsifiable in water, desirably to form clear liquid emulsions, are preferred. Such clear liquid emulsions can themselves be stable over time in certain embodiments. In certain embodiments, the addition of 0.3 mL of the herbicidal composition to 100 mL of water results in a clear liquid emulsion, which preferably remains a clear liquid emulsion for a period of at least 7 days when maintained at 0° C. In certain embodiments, the addition of 0.3 mL of the herbicidal composition to 100 mL of water results in a yellow or pale yellow clear liquid emulsion, which remains a yellow or pale yellow clear liquid emulsion for a period of greater than one hour when maintained at 0° C.

Herbicidal methods and compositions of the invention may be used in the complete or partial control of many noxious plants in terrestrial or aquatic environments. These include, for example, plants that are known aquatic weeds, including as examples common duckweed (*Lemna minor*), the emersed plants spatterdock (*Nuphar luteum*) and waterlily (*Nymphea* spp.), the submersed plants bladderwart (*Utricularia* spp.), common coontail (*Ceratophyllum demersum*), common elodea (*Elodea canadensis*), Brazilian elodea (*Egeria densa*), crested floating heart (*Nymphoides cristata*), fanwort (*Cabomba caroliniana*), hydrilla (*Hydrilla verticillata*), naiad (*Najas* spp.), pondweed (*Potamogeton* spp.) and more specifically curlyleaf pondweed (*Potamogeton crispus*), watermilfoil (*Myriophyllum* spp.) including Eurasian watermilfoil, floating plants including common watermeal (*Woffia columbiana*) and salvinia (*Salvinia* spp.), emersed plants including alligatorweed (*Alternanthera philoxeroides*), American lotus (*Nelumbo lutea*), cattail (*Typha* spp.), creeping waterprimrose (*Ludwidia peploides*), parrotfeather (*Myriophyllum aquaticum*), smartweed (*Polygonaum* spp.), spikerush (*Eleocharis* spp.), waterpurslane (*Ludwigia palustris*), and watershield (*Brasenia schreberi*), of the submersed plants Illinois pondweed (*Potamogeton illinoensis*), limnophila (*Limnophila sessiliflora*), tapegrass or American eelgrass (*Vallisneria americana*), and variable leaf watermilfoil (*Myriophyllum heterophyllum*), and the shoreline grasses barnyardgrass (*Echinochloa crusgalli*), and southern watergrass (*Hydrochloa caroliniensis*). Particularly preferred plant types for control in accordance with the invention include hydrilla, watermilfoil, watermeal, curlyleaf pondweed, crested floating heart, and Brazilian elodea.

When the herbicidal compositions of the invention are used as aquatic herbicides, bodies of water to be treated with the present invention will typically be fresh water bodies such as ponds, lakes, wet lands, reservoirs, rivers or irrigation canals, although other bodies of water may also be treated in accordance with this invention. The herbicidal composition can be added to the bodies of water in any suitable manner, including surface addition and/or subsurface addition (e.g. injection). As well, the herbicidal compositions of the invention can be applied "as is" to bodies of water, plants or to terrestrial or other environments to be herbicidally treated, or can be diluted by combination with another material such as a liquid medium, typically an aqueous liquid medium (e.g. water), and/or with another herbicide or herbicide formulation, prior to application.

In order to promote a further understanding of the present invention and its various embodiments, the following specific examples are provided. It will be understood that these examples are illustrative and not limiting of the invention.

Example 1

Herbicidal Composition Preparation

A homogenous solution is prepared by blending the ingredients specified in Table 1 in the amounts shown:

TABLE 1

| Ingredient | Percent (by weight) | Function |
|---|---|---|
| Fluridone | 6.3 | herbicide |
| Propylene Glycol | 36.1 | water-miscible solvent |
| N,N-dimethyloctamide, N,N-dimethyldecamide* | 47.0 | water-immiscible solvent |
| Butyl ethoxylate/propoxylate block copolymer** | 6.9 | nonionic surfactant |
| Dodceylbenzenesulfonic acid | 1.7 | anionic surfactant |
| 2-Ethyl-1-hexanol | 1.0 | surfactant (adjuvant) |
| Triethanolamine | 0.9 | surfactant |
| 30% Silicone Emulsion | 0.1 | antifoaming agent |
| Total | 100% | |

*Provided as Hallcomid M-8-10
**Provided as Toximul 8320

This formulation gives a colorless herbicidal formulation that exhibits the capacity to form an emulsion when diluted with water. When 0.3 mL of the formulation of the present example is added to 100 mL of water, the formed liquid emulsion is clear (non-cloudy) in appearance and was still clear 7 days after formation when stored at 0° C. As well, the herbicidal formulation itself is very stable to storage, demonstrating no phase separation when stored at 25° C. for at least 30 days in a sealed, fluid-tight inert container.

Example 2

Fluridone Uptake Study

Materials and Methods:

Studies were conducted to quantify potential differences in the initial uptake of the aquatic herbicide fluridone by the invasive submersed aquatic plant, *Hydrilla verticillata*. Apical meristems of dioecious hydrilla were collected from a stock plant culture. 10 cm apical segments were excised and placed in glass vials containing 50 mL of laboratory tap water. Each vial was then treated with a 10 µg/L theoretical dose of fluridone formulated as either Sonar® A.S. (available from SePRO Corporation, Carmel, Ind., 0.48 kg active ingredient per liter aqueous suspension-type formulation) or prepared according to Example 1 (0.06 kg active ingredient per liter). Each herbicide dose contained 40,000 DPM of $^{14}$C-labeled fluridone. Plants were harvested at 0, 6, 12, 24, and 48 hours after treatment. For each time point, the study design included five replications. Harvested plant tissue was dried for 48 hours at 60° C., measured for dry biomass, and then oxidized to determine counts of radioactivity. Herbicide uptake per unit dry biomass was determined based on the measured radioactivity, and formulation effect was analyzed through regression analysis. The study was conducted twice.

Results:

Results presented in FIG. 1 document an unexpectedly increased fluridone herbicide uptake by apical hydrilla tissue when delivered as prepared in the formulation of Example 1 compared to the Sonar® A.S. formulation. Uptake was about 20% greater for the formulation of Example 1-treated hydrilla versus Sonar® A.S.-treated hydrilla at 24 hours and about 30% greater for the formulation of Example 1 over the Sonar® A.S. formulation at 48 hours. These controlled study results agree with qualitative field observations suggesting faster symptomology and control of target vegetation with the formulation of Example 1 versus the Sonar® A.S. formulation.

The uses of the terms "a" and "an" and "the" and similar references in the context of describing the invention (especially in the context of the following claims) are to be construed to cover both the singular and the plural, and was otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., such as) provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A herbicidal composition, comprising:
   fluridone, in an amount of about 5% to about 11% by weight of the composition;
   one or more water-immiscible organic solvents, the one or more water-immiscible organic solvents constituting about 35% to about 55% by weight of the composition, and wherein said one or more water-immiscible organic solvents comprise N,N-dimethyloctamide and/or N,N-dimethyldecamide;
   one or more water-miscible organic solvents, the one or more water-miscible organic solvents constituting about 20% to about 45% by weight of the composition, and where said one or more water-miscible organic solvents comprise propylene glycol;
   an emulsifying surfactant system including at least one nonionic surfactant and at least one anionic surfactant, wherein said at least one nonionic surfactant comprises a butyl ethoxylate/propoxylate block copolymer and wherein said at least one anionic surfactant comprises dodecylbenzenesulfonic acid or a salt thereof.

2. The composition of claim 1, wherein:
the fluridone is present in an amount of about 5% to about 9% by weight of the composition;
the one or more water-immiscible organic solvents constitute about 45% to about 55% by weight of the composition; and
the one or more water-miscible organic solvents constitute about 30% to about 40% by weight of the composition.

3. The composition of claim 1, wherein the composition is substantially free from water.

4. The composition of claim 1, wherein the composition is a substantially homogenous solution.

5. A herbicidal composition, comprising:
fluridone, in an amount of about 3% to about 15% by weight of the composition;
one or more water-immiscible organic solvents, wherein the one or more water-immiscible organic solvents include N,N-dimethyloctanamide and/or N,N-dimethyldecanamide, and wherein the one or more water-immisicible organic solvents constitute about 20% to about 60% of the composition by weight;
one or more water-miscible organic solvents, wherein the one or more water-miscible organic solvents constitute about 20% to about 60% of the composition by weight; and
an emulsifying surfactant system, wherein the emulsifying surfactant system includes at least one anionic surfactant and at least one nonionic surfactant; and
wherein said herbicidal composition remains clear without any phase separation for a period of greater than one day when maintained in a sealed-fluid tight inert container at 25° C.

6. The composition of claim 5, wherein the fluridone constitutes about 3% to about 9% by weight of the composition.

7. The composition of claim 5, which is substantially free from water.

8. The composition of claim 5, wherein the composition is a substantially homogeneous solution.

9. A method for herbicidally treating a plant submersed in water or its supporting environment with fluridone, comprising applying to the submersed plant or its supporting environment (i) the composition of claim 1, or (ii) a composition prepared by combining the composition of claim 1 with another substance, wherein said environment is a body of water.

10. A herbicidal composition, comprising:
fluridone, in an amount of about 5% to about 11% by weight of the composition;
N,N-dimethyloctanamide, N,N-dimethyldecanamide, or a mixture thereof, in an amount constituting at least 50% by weight of all water-immiscible solvents in the composition;
propylene glycol, in an amount constituting at least about 50% by weight of all water-miscible organic solvents in the composition;
an emulsifying surfactant system including at least one anionic surfactant and at least one nonionic surfactant; and
an antifoaming agent; and
wherein said herbicidal composition remains clear without any phase separation for a period of greater than one day when maintained in a sealed-fluid tight inert container at 25° C.

11. The herbicidal composition of claim 10, wherein the at least one nonionic surfactant comprises a butyl ethoxylate/propoxylate block copolymer and wherein said at least one anionic surfactant comprises dodecylbenzenesulfonic acid or a salt thereof.

12. The herbicidal composition of claim 10, wherein N,N-dimethyloctanamide, N,N-dimethyldecanamide, or a mixture of N,N-dimethyloctanamide and N,N-dimethyldecanamide, constitutes at least 75% by weight of all water-immiscible solvents in the composition.

13. The herbicidal composition of claim 12, wherein N,N-dimethyloctanamide, N,N-dimethyldecanamide, or a mixture thereof, constitutes at least 90% by weight of all water-immiscible solvents in the composition.

14. The herbicidal composition of claim 10, wherein propylene glycol constitutes at least 75% by weight of all water-miscible solvents in the composition.

15. The herbicidal composition of claim 14, wherein propylene glycol constitutes at least 90% by weight of all water-miscible solvents in the composition.

16. The herbicidal composition of claim 15, wherein the at least one nonionic surfactant comprises a butyl ethoxylate/propoxylate block copolymer and wherein said at least one anionic surfactant comprises dodecylbenzenesulfonic acid or a salt thereof.

\* \* \* \* \*